United States Patent [19]

Luther

[11] Patent Number: 4,842,591
[45] Date of Patent: Jun. 27, 1989

[54] CONNECTOR WITH ONE-WAY SEPTUM VALVE, AND ASSEMBLY

[76] Inventor: Ronald B. Luther, 530 Kings Rd., Newport Beach, Calif. 92663

[21] Appl. No.: 146,718

[22] Filed: Jan. 21, 1988

[51] Int. Cl.[4] ............................................. A61M 25/00
[52] U.S. Cl. .................................... 604/283; 604/905; 285/3
[58] Field of Search ............... 604/207, 206, 205, 202, 604/201, 200, 283, 280, 905, 87, 88, 244; 285/3

[56] References Cited

U.S. PATENT DOCUMENTS

| | | | |
|---|---|---|---|
| 4,013,310 | 3/1977 | Dye | 604/283 X |
| 4,511,359 | 4/1985 | Vaillancourt | 604/905 X |
| 4,559,043 | 12/1985 | Whitehouse et al. | 604/201 |
| 4,720,285 | 1/1988 | Pickhard | 604/206 X |

*Primary Examiner*—John D. Yasko
*Attorney, Agent, or Firm*—Willie Krawitz

[57] ABSTRACT

A one-way septum valve in a connector device to maintain sterility is provided. The device prevents the backward flow of blood and body fluids through the connector to an injection device such as a syringe, I.V. unit, and the like.

The valve includes a slit, resilient septum mounted within the connector, and a moveable plug spaced a short distance from the septum and adapted to move forward slightly upon contact with the injection device.

When the injection device is moved forward, it will contact and drive the plug a short distance into the septum causing it to open and deform inwardly. This enables fluid from the I.V. unit, syringe, etc., to be fed through the septum opening and into a patient. When the injection device is retracted out of contact with the plug, the septum resiliency forces the plug back out of the septum which then closes and seals. Any reverse pressure of blood or body fluid will cause the septum to move outwardly into contact with the plug, which will prevent further movement of the septum. Hence, the septum becomes, in effect, a one-way valve.

7 Claims, 2 Drawing Sheets

CONNECTOR WITH ONE-WAY SEPTUM VALVE, AND ASSEMBLY

BACKGROUND OF THE INVENTION

This invention relates to a new and improved connector device having a one-way septum valve. Connector devices employing septum seals are used to provide a sterile closure for use with I.V. and syringe systems; the seals also prevent blood leakage from the patient and back through the connector. However, the prior art connectors tend to be complicated and, hence, expensive and not always effective.

It would be desireable to provide a simple and inexpensive assembly of a connector for an I.V. unit, syringe, and the like, including a septum seal having good sealing and sterility properties and which can be used a number of times while still maintaining these properties.

THE INVENTION

According to the invention, a connector and assembly for an I.V. unit, syringe, and the like is provided including a deformable slit septum including a sterile and liquid seal for the connector. A moveable, hollow plug is positioned a short distance from the septum and is adapted to deform and enter the septum slit and maintain the slit open during use. Hence, when contact is made between the plug and the syringe tip, the plug will enter the slit of the septum and outwardly deform the septum slightly. This permits liquid to flow through the septum to the patient.

Following use, when the syringe tip is withdrawn from contact with the plug, support for the plug will thereby be removed. Consequently, the septum will deform to its initial closed state and force the plug out to its original position. This will cause
the septum to reseal and prevent the backward flow of blood, etc., from the patient through the connector. In the retracted position, the syringe tip will just contact or be spaced a very short distance from the plug. The entry of the plug into the septum and its retraction can be repeated a number of times without necessitating replacement of the connector, and while still maintaining a sterile seal.

Figure 1:
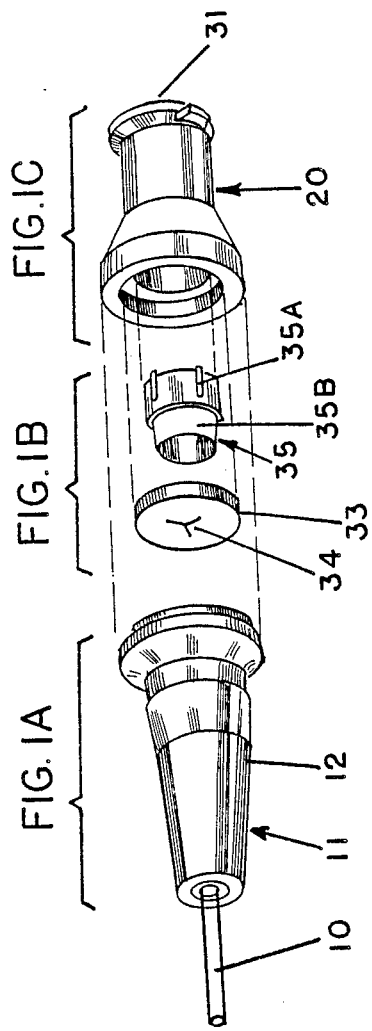
FIGS. 1A, B and C are exploded, external perspective views showing the disassembled components of the device.

DESCRIPTION OF THE PREFERRED EMBODIMENTS:

The connector 9 of this invention may be of plastic or metal and is shown comprising a hollow proximal end fitting 11 which connects to a catheter 10 for feeding liquid into a patient. The proximal fitting 11 includes a nozzle portion 12 providing an internal bore 13 which is parallel or slightly tapered to form a tight fit with the catheter. The nozzle portion 12 may be integrally formed with the fitting or it may be formed separately as a tube which is secured by heat, threading, etc., to the fitting 11. The rear portion of the fitting 11 has an outer, circumferential body 14 defining circular faces 15, 16 and 17. The body 14 has an enlarged bore 18 which tapers down to merge with the internal bore 13 of the nozzle portion 12.

A distal fitting 20 comprises a forward end 21 which is attached, by say threading, or as shown, by heat welding to the proximal end fitting 11 along a circular sealing bead 22 on the face 15 of fitting 11. The distal fitting 20 includes circular faces 23, 24 and 25, with faces 23 and 24 contacting corresponding faces 15 and 16 of fitting 11. A bore 26 is defined longitudinally of the distal fitting 20 and has a circular seating shoulder 27 at its rearward end that functions as a stop for a moveable plug which will be defined in more detail, infra. The bore 26 has a slightly enlarged tapered bore portion 28 to provide a tight fit with a luer tip, syringe, etc. A flange 31 is formed at the end of the distal fitting 20 to engage with a luer locking type of device.

A space 32 is formed between the faces 17 and 25, respectively of the proximal fitting 11 and distal fitting 20, and a resilient septum 33 is fitted into this space. The septum is slit 34 so that it can be deformed by a moveable plug 35 which rests in the bore 26 of fitting 20, or deformed open by a needle.

The moveable plug 35 defines longitudinal ribs 35a to maintain uniform contact with the bore 26 in the distal fitting, and it has a forward, tubular portion 35b to facilitate entry into the septum slit 34. The rear portion of the moveable plug is recesed 36 to contact the tip 37 of a syringe 38 which fits into the tapered bore portion 28 of the bore 26. Prior to penetration of the plug into the septum, a typical plug spacing is about 0–10 mils from the septum; this spacing prevents the septum from moving backwards and leaking blood or fluid from the patient.

Figure 2:
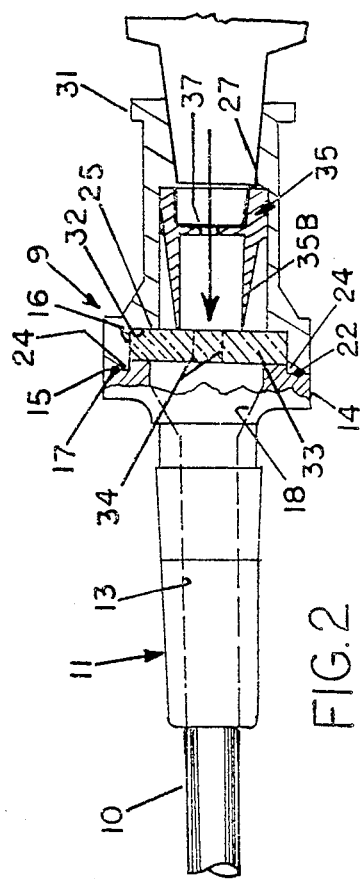
FIG. 2 is a sectional view in side elevation showing the assembled device.
Figure 3:
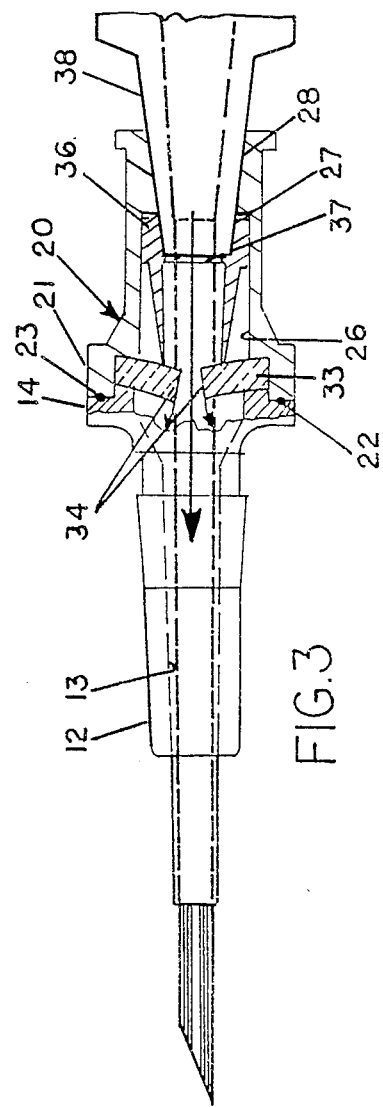
FIG. 3 is a sectional view in side elevation showing the assembled device, with the septum portion being open for liquid flow.

As shown in FIG. 3, when the syringe tip 37 is inserted into the tapered bore portion 28, it will contact the moveable plug 35 and move it forwardly until it just deforms the septum. Liquid is injected through the septum and into the patient, following which the syringe tip is withdrawn out of contact with the plug. Since support for the plug has now been removed, the resiliency of the septum will force the plug back to its initial position, as shown in FIG. 2, and the septum will reseal itself. The process can be repeated many times, and the connector functions as a one-way valve while still maintaining sterility under lead proof conditions. This of course reduces the cost of replacing a connector every time a separate injection is made.

I claim:

1. A connector with a one-way septum valve, including:
   (a.) a proximal portion having a forward bore for mounting a catheter therein, the proximal portion being enlarged rearwardly for seating a deformable, slit septum;
   (b.) a distal portion attached to the proximal portion, and securing the said septum therebetween, the distal portion defining a rearward bore for engaging a syringe, I.V. unit, and the like, and for securing a moveable plug therein;
   (c.) a hollow, moveable plug secured in the rearward bore of the distal portion, the plug being positioned adjacent the septum; whereby:
      i. the plug is adapted to be moved forwardly within the bore upon contact with the I.V. unit, syringe, and the like at a tip thereof, and then to enter the septum slit and deform the septum open;

ii. liquid from the I.V. unit, syringe, and the like will pass through the connector to a patient when the septum is open;

iii. when the I.V. unit, syringe and the like is withdrawn from the patient, the septum will deform to its closed position and force the plug back along the bore of the distal portion; and, iv. the plug is adapted to support the septum against liquid flow from the patient through the connector, thereby maintaining the connector in a leak proof and sterile manner after repeated use.

2. The connector of claim 1, in which the plug is positioned about 0–10 mils adjacent from the septum.

3. The connector of claim 1, in which the plug includes external, longitudinal ribs to maintain uniform contact between the plug and the bore of the distal fitting.

4. The connector of claim 1, in which the distal bore defines a seating shoulder to position the plug adjacent the septum.

5. The connector of claim 1, including the assembly with and I.V. unit, syringe, and the like.

6. The connector of claim 1, including a catheter mounted in the forward bore of the proximal connector.

7. The connector of claim 6, in which a needle deforms open the septum and is positioned through the catheter.

* * * * *